US00PP27291P2

(12) United States Plant Patent
Hooijman

(10) Patent No.: US PP27,291 P2
(45) Date of Patent: Oct. 25, 2016

(54) ROSE PLANT NAMED 'ESM R129'

(50) Latin Name: *Rosa hybrida*
Varietal Denomination: ESM R129

(71) Applicant: Aloysius A. J. Hooijman, Aalsmeer (NL)

(72) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 184 days.

(21) Appl. No.: 14/121,546

(22) Filed: Sep. 17, 2014

(51) Int. Cl.
*A01H 5/02* (2006.01)

(52) U.S. Cl.
USPC ..... Plt./140

(58) Field of Classification Search
USPC ..... Plt./140
See application file for complete search history.

*Primary Examiner* — Keith Robinson
(74) *Attorney, Agent, or Firm* — C. A. Whealy

(57) ABSTRACT

A new and distinct cultivar of Rose plant named 'ESM R129', characterized by its upright, long and strong flowering stems; vigorous growth habit and high productivity; dark green-colored leaves; red-colored flowers that are typically grown as single-stem types; and excellent postproduction longevity.

1 Drawing Sheet

Botanical designation: *Rosa hybrida.*
Cultivar denomination: 'ESM R129'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'ESM R129'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in February, 2008 of a proprietary Rose selection identified as Line 42, not patented, as the female, or seed, parent with a proprietary Rose selection identified as Line 406, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in May, 2009.

Asexual reproduction of the new Rose plant by bud grafting in El Quinche, Pichincha, Ecuador since March, 2010 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R129'. These characteristics in combination distinguish 'ESM R129' as a new and distinct Rose plant:

1. Upright, long and strong flowering stems.
2. Vigorous growth habit and high productivity.
3. Dark green-colored leaves.
4. Red-colored flowers that are typically grown as single-stem types.
5. Excellent postproduction longevity.

Plants of the new Rose differ from plants of the female parent selection in the following characteristics:

1. Plants of the new Rose have longer flowering stems than plants of female parent selection.
2. Flowers of plants of the new Rose have more petals than flowers of plants of the female parent selection.
3. Flowers of plants of the new Rose are longer-lasting than flowers of plants of the female parent selection.

Plants of the new Rose differ from plants of the male parent selection in the following characteristics:

1. Plants of the new Rose produce more flowering stems than plants of the male parent selection.
2. Flowers of plants of the new Rose are longer-lasting than flowers of plants of the male parent selection.

Plants of the new Rose can be compared to plants of *Rosa hybrida* 'Freedom', not patented. In side-by-side comparisons conducted in El Quinche, Pichincha, Ecuador, plants of the new Rose differed from plants of 'Freedom' in the following characteristics:

1. Plants of the new Rose had longer and stronger flowering stems than plants of 'Freedom'.
2. Plants of the new Rose were more vigorous than plants of 'Freedom'.
3. Plants of the new Rose had fewer thorns than plants of 'Freedom'.
4. Plants of the new Rose had larger flower buds than plants of 'Freedom'.

5. Flowers of plants of the new Rose were longer-lasting than flowers of plants of 'Freedom'.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph on the left side of the sheet comprises a side perspective view of a typical flowering stem of 'ESM R129'.

The photograph at the upper right of the sheet is a close-up view of a typical developed flower of 'ESM R129'.

The photographs at the lower right of the sheet are close-up views of the upper and lower surfaces of typical leaves of 'ESM R129'.

DETAILED BOTANICAL DESCRIPTION

The aforementioned photographs, following observations and measurements describe plants grown in 10-liter containers in a polyethylene-covered greenhouse in El Quinche, Pichincha, Ecuador and under typical hydroponic Rose production practices. Plants were pinched 13 to 14 weeks after planting and were two years and 47 weeks old when the description and photographs were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'ESM R129'.

Parentage:

*Female, or seed, parent*.—Proprietary seedling selection of *Rosa hybrida* identified Line 42, not patented.

*Male, or pollen, parent*.—Proprietary seedling selection of *Rosa hybrida* identified Line 406, not patented.

Propagation:

*Type*.—By bud grafting.

*Time to initiate roots, summer*.—About 15 days at temperatures about 26° C. to 30° C.

*Time to produce a rooted young plant, summer*.—About 30 days at temperatures about 22° C. to 26° C.

*Root description*.—Fibrous, medium in thickness; close to N199B in color.

*Rooting habit*.—Moderately freely branching; medium density to dense.

Plant description:

*Plant and growth habit*.—Perennial shrub; upright and strong flowering stems; typically grown as a single-stem type cut flower; vigorous growth habit.

*Branching habit*.—Freely basal branching habit; highly productive with about 11.5 flowering stems developing per plant per year.

*Plant height*.—About 180 cm.

*Plant width* (*spread*).—About 60 cm.

*Lateral branches*.—Quantity: About eleven lateral branches develop per plant. Length: About 94 cm. Diameter: About 8 mm. Internode length: About 5 cm. Texture: Smooth, glabrous; older stems, woody. Color: Close to N199B. Thorns: Density: Medium. Shape: Triangular with sharp acuminate apices; slightly incurved and flat. Height: About 8 mm. Length, at base: About 1.1 cm. Color, immature: Close to 187C and 153D. Color, mature: Close to 184A and 162A.

Leaf description:

*Arrangement*.—Alternate; compound with typically five to seven leaflets per leaf.

*Leaf length*.—About 20.5 cm.

*Leaf width*.—About 12.8 cm.

*Terminal leaflet length*.—About 6.7 cm.

*Terminal leaflet width*.—About 4.2 cm.

*Lateral leaflet length*.—About 6.2 cm.

*Lateral leaflet width*.—About 3.7 cm.

*Leaflet shape*.—Ovate.

*Leaflet apex*.—Acuminate.

*Leaflet base*.—Attenuate.

*Leaflet margin*.—Serrate.

*Leaflet texture, upper and lower surfaces*.—Smooth; papery to coriaceous.

*Leaflet venation pattern*.—Pinnate.

*Leaflet color*.—Developing leaflets, upper surface: Close to 147A. Developing leaflets, lower surface: Close to 148B and 183D. Fully expanded leaflets, upper surface: Close to between 139A and 147A; venation, close to 152D. Fully expanded leaflets, lower surface: Close to 147B; venation, close to 152D.

*Petioles, leaves*.—Length: About 1.3 cm. Diameter: About 1.8 mm. Texture, upper surface: Prickly. Texture, lower surface: Smooth, glabrous. Color, upper surface: Close to 199A, 146A and 187B. Color, lower surface: Close to 152B and 144A.

*Petioles, leaflets*.—Length: About 3.5 cm. Diameter: About 1 mm. Texture, upper surface: Prickly. Texture, lower surface: Smooth, glabrous. Color, upper surface: Close to 146A and 187A. Color, lower surface: Close to between 146C and 144A.

*Stipules*.—Arrangement and appearance: Two, adnate to the petiole, leafy in appearance. Length: About 3.25 cm. Width: About 2 mm. Shape: Roughly deltoid. Apex: Acuminate, tapered. Base: Tapered. Margin: Serrate. Texture, upper and lower surfaces: Smooth; membranous. Venation pattern: Pinnate. Color, upper surface: Close to 146A to 146C. Color, lower surface: Close to 144A.

Flower description:

*Flower type and arrangement*.—Symmetrical rosette flowers; flowers typically grown as single-stem types; flowers face upright.

*Flowering season*.—Plants of the new Rose flower year-round under greenhouse conditions; early flowering habit, plants begin flowering about 73 days after pinching.

*Flower diameter*.—About 11.5 cm.

*Flower depth* (*height*).—About 6.1 cm.

*Flower longevity*.—Excellent postproduction longevity; flowers maintain good substance for about 26 to 28 days on the plant and for about 15 to 17 days as cut flowers; flowers persistent.

*Fragrance*.—None detected.

*Flower buds*.—Length: About 5.7 cm. Diameter: About 5 cm. Shape: Ovoid. Rate of opening: About 14 to 15 days. Color: Towards the apex, close to 183B; towards the base, close to 144A.

*Petals*.—Quantity: About 46 per flower; petals imbricate. Length: About 6.4 cm. Width: About 6.6 cm. Shape: Nearly round to transversely ovate. Apex: Short acute. Base: Obtuse. Margin: Entire or slightly and irregularly lobed. Texture, upper and lower surfaces: Smooth, glabrous; papery to coriaceous. Color: When opening, upper surface: Close to 53A; towards the base, close to 154D. When opening, lower surface: Close to 60A; towards the base, close to 154D. Fully opened, upper and lower surfaces: Close to 46A; towards the base, close to 150D.

*Petaloids*.—Quantity: About three; whorled. Length: Variable. Width: Variable. Shape: Irregularly shaped. Apex: Short acute. Base: Obtuse. Margin: Mostly uneven. Texture, upper and lower surfaces: Smooth, glabrous; papery to coriaceous. Color: When opening, upper and lower surfaces: Close to 53A and 157D; towards the base, close to 154C. Fully opened, upper and lower surfaces: Close to 53A and 157D; towards the base, close to 155A.

*Sepals*.—Quantity per flower: Typically five in a single whorl. Length: About 5.6 cm. Width: About 1.4 cm. Shape: Roughly deltoid. Apex: Tapered. Base: Truncate. Margin: Entire; ciliated and/or glandular. Texture, upper and lower surfaces: Leathery; rugose. Color: When opening, upper surface: Close to between 145A and 146C. When opening, lower surface: Close to between 144A and 146A. Fully opened, upper surface: Close to between 146C and 145C. Fully opened, lower surface: Close to 144A and N199C.

*Reproductive organs*.—Stamens: Quantity: About 111 per flower. Anther length: About 4 mm. Anther shape: Reniform. Anther color: Close to 163B. Filament color: Close to 53D. Pollen amount: Moderate to abundant. Pollen color: Close to 163B. Pistils: Quantity: About 194 per flower. Pistil length: About 2 cm. Stigma shape: Broadly reniform. Stigma color: Close to 160B. Style length: About 1.4 cm. Style color: Close to 154D. Receptacle height: About 1.1 cm. Receptacle diameter: About 1 cm. Receptacle shape: Cup-shaped. Receptacle texture: Smooth, glabrous. Receptacle color: Close to 145A. Fruits and seeds: Fruit and seed development have not been observed on plants of the new Rose.

Pathogen & pest tolerance: Plants of the new Rose have not been observed to be tolerant to specific pathogens and pests common to Rose plants.

Temperature tolerance: Plants of the new Rose have been observed to tolerate temperatures ranging from 0° C. to 35° C.

It is claimed:

1. A new and distinct Rose plant named 'ESM R129' as illustrated and described.

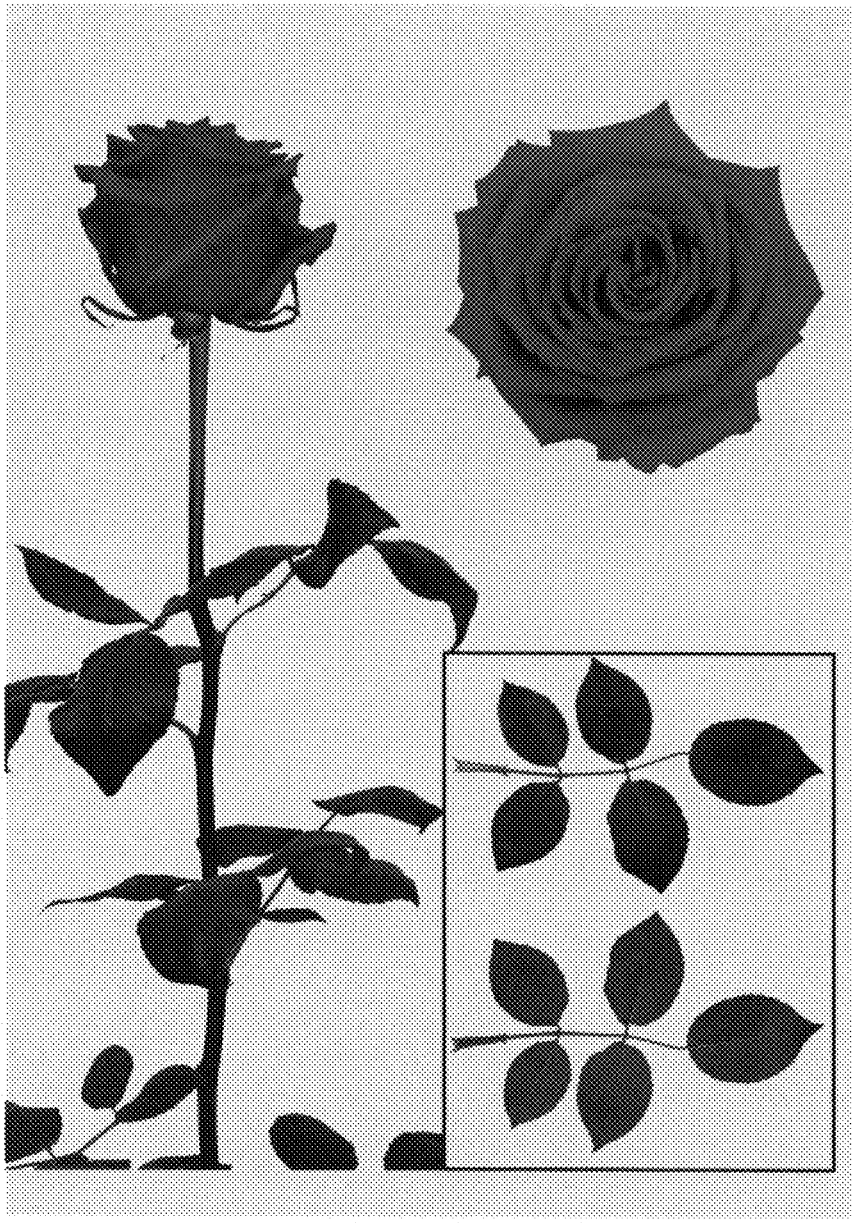

* * * * *